United States Patent [19]
Cerwin et al.

[11] Patent Number: 6,029,806
[45] Date of Patent: Feb. 29, 2000

[54] PACKAGE FOR DOUBLE-ARMED SUTURES

[75] Inventors: Robert J. Cerwin, Pipersville, Pa.;
Peter Konarnycky, Lebanon, N.J.;
Connie Roshdy, New Egypt, N.J.; Alex Ilori, Flemington, N.J.

[73] Assignee: Ethicon, Inc., Somerville, N.J.

[21] Appl. No.: 09/268,030

[22] Filed: Mar. 15, 1999

[51] Int. Cl.$^7$ .................................................. A61B 17/06
[52] U.S. Cl. ........................ 206/63.3; 206/227; 206/380; 53/118; 53/430
[58] Field of Search ........................... 206/63.3, 380–382, 206/227, 495; 53/118, 430

[56] References Cited

U.S. PATENT DOCUMENTS

| | | | |
|---|---|---|---|
| 4,034,850 | 7/1977 | Mandel et al. . | |
| 4,063,638 | 12/1977 | Marwood | 206/63.3 |
| 4,120,395 | 10/1978 | Mandel et al. | 206/63.3 |
| 4,615,435 | 10/1986 | Alpern et al. | 206/63.3 |
| 4,699,271 | 10/1987 | Lincoln et al. . | |
| 4,946,043 | 8/1990 | Roshdy et al. | 206/63.3 |
| 4,967,902 | 11/1990 | Sobel et al. . | |
| 5,230,424 | 7/1993 | Alpern et al. . | |
| 5,249,673 | 10/1993 | Sinn . | |
| 5,871,089 | 2/1999 | Odermatt | 206/63.3 |

*Primary Examiner*—Paul T. Sewell
*Assistant Examiner*—Luan K. Bui
*Attorney, Agent, or Firm*—Selitto & Associates

[57] ABSTRACT

A suture package includes a base panel with a needle park and a plurality of pockets having plural compartments stacked in the Z direction. The package is suitable for containing and dispensing a plurality of double-armed sutures during time-critical surgery and promotes tangle-free dispensing by winding the sutures through the compartments in a serpentine manner to avoid suture-to-suture interaction. Spatial separation of the needles in the needle park and color coding of the sutures allows for easy identification of the individual sutures during dispensing and when tying off the sutures during surgery.

20 Claims, 5 Drawing Sheets

PACKAGE FOR DOUBLE-ARMED SUTURES

FIELD OF THE INVENTION

The present invention relates to packages for double-armed sutures, and, more particularly, to packages for multiple double-armed sutures wherein each suture may include a pledget centered thereon and is removable from the package without tangling or knotting.

BACKGROUND OF THE INVENTION

Double-armed sutures, i.e., a surgical suture with a needle at each end, are well known and commonly used, e.g., in cardiovalve replacement surgery. This type of suture is optionally manufactured with a pre-centered pledget, i.e., a cushioning pad to prevent the suture from cutting into the tissue, which is also known in the art. Such sutures are frequently packaged in sets to supply an adequate number to advance the surgery without requiring opening and handling multiple packages. The sutures are typically arranged in the package with the needle ends of each suture grouped together such that the two ends of each suture can be identified. It is preferable for the package to be able to dispense each suture by grasping one or both of the associated needles with a needle holder. Prior art packages for multiple double-armed sutures are exemplified by U.S. Pat. No. 4,034,850, which is incorporated herein by reference for its disclosure of suture packaging methods and apparatus. The package disclosed in the '850 patent winds the individual sutures within the package in a figure eight pattern.

During surgery, a rhythm is developed between the scrub nurse and the surgeon in passing the sutures to the surgeon. If a suture becomes tangled upon removal from the package, this rhythm is interrupted and lengthens the surgery, which poses a danger to the patient. Accordingly, it remains an objective in this field to provide suture packaging that minimizes the chances of suture tangling.

Surgeons variously prefer to handle either a single needle holder, which is sequentially used to grasp and insert a first needle of the suture then the second needle, or a pair of needle holders, which are used for simultaneously grasping both needles. It is desirable for each needle to be presented in the package with adequate space around it for the scrub nurse to readily grasp each needle individually with a needle holder. Spatial separation of the needles must not disturb their visual grouping, i.e., it must be apparent which two needles are connected to the same suture. Furthermore, spatial separation of the needles cannot be allowed to appreciably enlarge the needle package to the degree that it becomes unwieldy or that it cannot be accommodated in the standard storage devices present in the operating room and supply cabinets.

It is therefore an object of the present invention to provide a new and improved package for multiple double-armed sutures that prevents tangling of the sutures and, on sutures so supplied, keeps a pledget centered on the suture upon withdrawal from the package. It is also desirable to have a package that is easy to handle, yet is capable of holding multiple sutures. Another object of the invention is to provide a package that applies minimal compression pressure to the sutures, such that the sutures are loose within the package, and are therefore easy to remove.

SUMMARY OF THE INVENTION

A suture package constructed in accordance with the present invention includes a base panel with a needle park disposed thereon. A first cover sheet is positioned on the base panel, and a second cover sheet is positioned on top of the first cover sheet. The second cover sheet is attached to the first cover sheet and the first cover sheet is attached to the base panel to form a multi-compartment pocket which has a first compartment located between the base panel the said first cover sheet, and a second compartment located between the first cover sheet the said second cover sheet. A suture having at least one needle is removably retained in the needle park, the suture also having a first portion, which is positioned in the first compartment, and a second portion, which is positioned in the second compartment.

BRIEF DESCRIPTION OF THE FIGURES

For a better understanding of the present invention, reference is made to the following detailed description of two exemplary embodiments considered in conjunction with the accompanying drawings, in which.

DETAILED DESCRIPTION OF THE FIGURES

Figure 1:
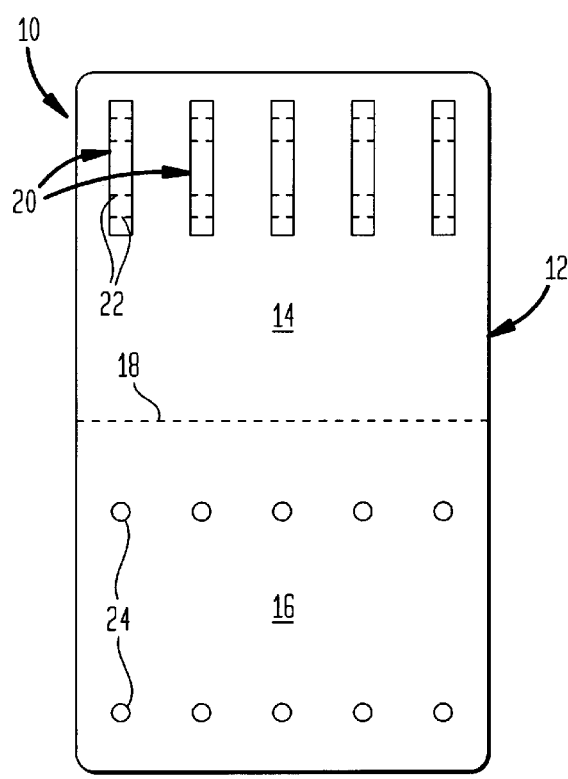
FIG. 1 is a plan view of a folder common to both exemplary embodiments of the present invention.

Referring now to FIG. 1, a suture package 10 designed for use in connection with sutures of a particular length, e.g., 30 inches, includes a folder 12, which serves as a base panel upon which the suture package 10 is built and which is common to both embodiments described hereinbelow. The folder 12 consists of an upper section 14 and a lower section 16, which are separated by a fold line 18. The upper section 14 includes a plurality of needle parks 20, which are each preferably in the form of a foam strip. Each needle park 20 includes four slits 22, each slit designed to accommodate one needle of a suture. The lower section 16 includes a plurality of holes 24.

Figure 2:
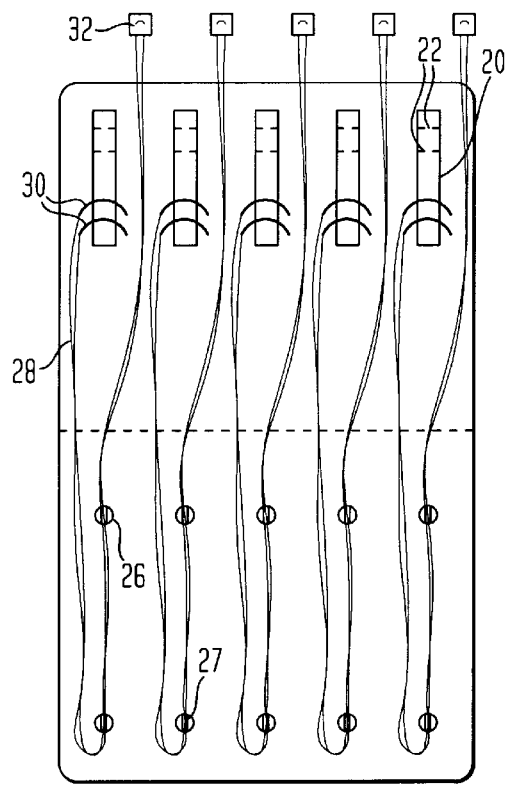
FIGS. 2–7 show diagrammatic views of the steps involved in fabricating a first embodiment of the present invention.

As shown in FIG. 2, for assembly of the suture package 10, the folder 12 is placed onto a suture winding jig (not shown) which includes a plurality of first pins 26 and second pins 27, the pins 26, 27 passing through the corresponding holes 24 in the lower section 16. Each of the pins 26, 27 is split, having a central slit extending therethrough, to allow a suture to be threaded through the middle of the pin. Each of the pins 26, 27 may also include an inwardly biased spring member, to grip a suture threaded into the slit of the pin. A suture 28 includes two needles 30, one needle 30 at each end of the suture 28. A pledget 32 is centered along the length of the suture 28.

The remainder of the discussion regarding the assembly of the suture package shall describe the insertion of a single suture into each set of the package. This description is equally applicable to each of the sutures positioned in the same set.

Still referring to FIG. 2, the needles 30 of a suture 28 are placed into two adjacent slits 22 of the needle park 20. The suture 28 is passed to the left side of the first pin 26 and to the left side of the second pin 27. The suture 28 is then threaded through the slit in the second pin 27 and through the slit in the first pin 26, with the pledget 32 being placed to the right of the needle park 20.

Figure 3:
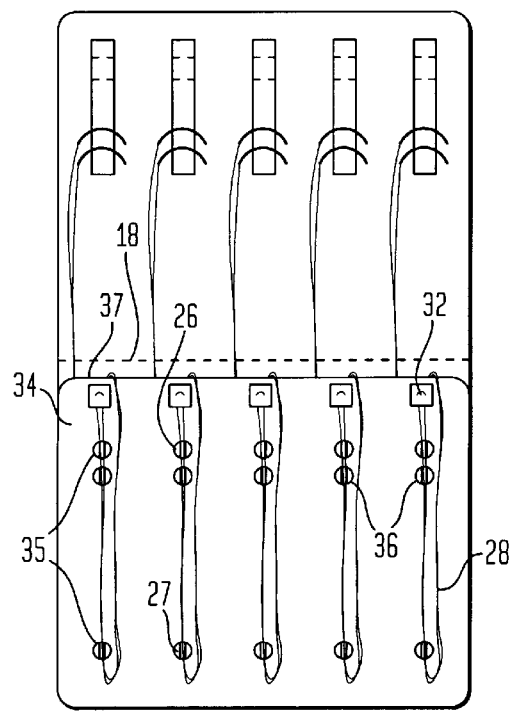

In FIG. 3, a first cover sheet 34, having a plurality of holes 35 corresponding to the holes 24 in the lower section 16, is placed onto the jig, with the first and second pins 26, 27 passing through the holes 35. An extraneous set of holes 36 is provided in the first cover sheet 34 because the sheet 34 may have dual use, e.g., in fabricating a suture package with different suture lengths and/or using a suture winding jig with pins that are spaced differently than that illustrated in FIGS. 1 and 2. The pledget 32 is picked up and the suture 28 is passed to the right of the first and second pins 26, 27 and on top of the first cover sheet 34. The suture 28 is threaded through the slit in the second pin 27 and then through the slit in the first pin 26, with the pledget 32 resting on top of the first cover sheet 34, proximate to but spaced from an upper edge 37 thereof.

Figure 4:
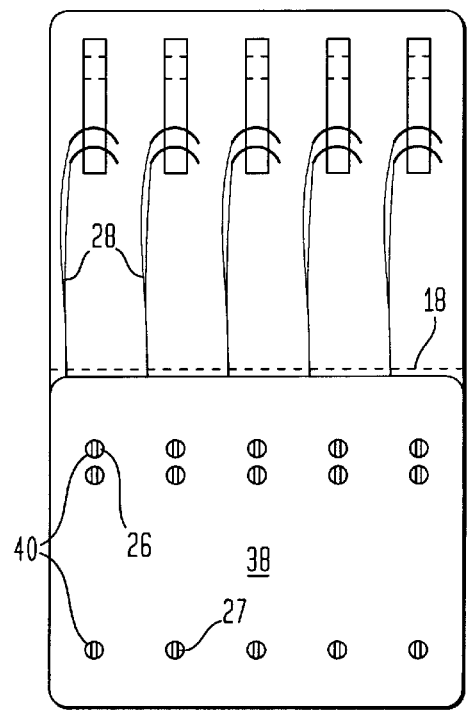

Referring now to FIG. 4, a second cover sheet 38 having a plurality of holes 40 is placed onto the jig. The first and second pins 26, 27 align with the holes 40. The second cover sheet 38 is dimensioned slightly larger than the first cover sheet 34, such that the second cover sheet 40 extends adjacent to the fold line 18 of the folder 12 and covers the sutures 28 and the pledgets 32 of the first set of sutures.

Figure 5:
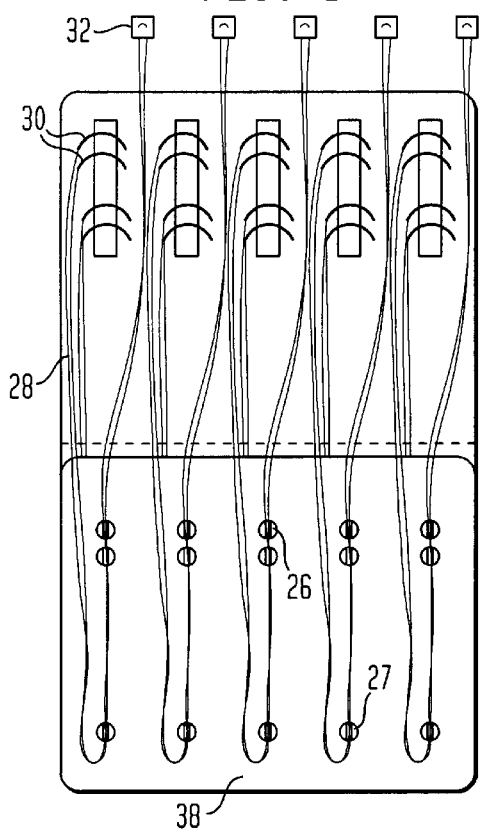

FIG. 5 shows the first step of packaging the second set of sutures 28. The needles 30 of a suture 28 are placed into the two empty, upper slits 22 of the needle park 20. The suture 28 is passed to the left side of the first pin 26, to the left side of the second pin 27, and on top of the second cover sheet 38. The suture 28 is then threaded through the slit in the second pin 27 and through the slit in the first pin 26, with the pledget 32 being placed to the right of the needle park 20.

Figure 6:
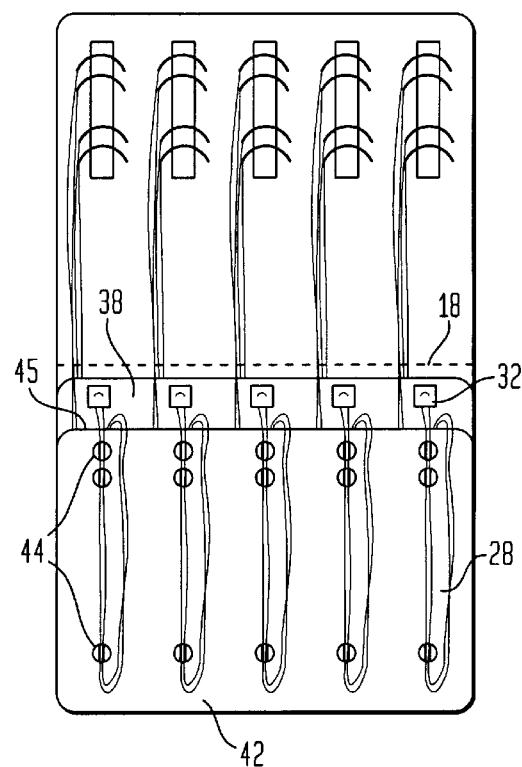

As shown in FIG. 6, a third cover sheet 42, having a plurality of holes 44 corresponding to the holes 40 in the second cover sheet 38, is placed onto the jig, with the first and second pins 26, 27 passing through the holes 44. The third cover sheet 42 is dimensioned smaller than the second cover sheet 38, such that an upper edge 45 of the third cover sheet 42 is spaced away from the fold line 18 of the folder 12, leaving an area of the second cover sheet 38 that is not covered by the third cover sheet 42. This provides additional space for the pledget 32 as shall be seen below.

The pledget 32 is picked up and the suture 28 is passed to the right of the first and second pins 26, 27 and on top of the third cover sheet 42. The suture 28 is threaded through the slit in the second pin 27 and then through the slit in the first pin 26, with the pledget 32 resting on top of the second cover sheet 38, in between the fold line 18 of the folder 12 and the upper edge 45 of the third cover sheet 42.

Figure 7:
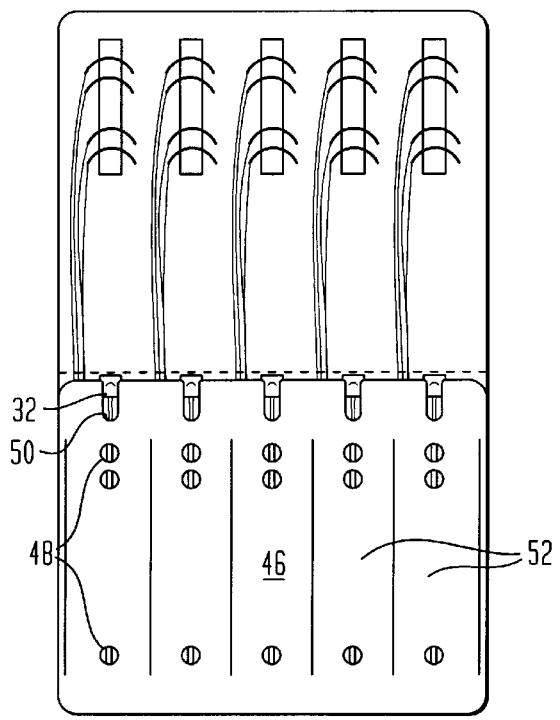

Referring now to FIG. 7, a fourth cover sheet 46 having a plurality of holes 48 is placed onto the jig, with the pins 26, 27 passing through the holes 48. The fourth cover sheet 46 includes a plurality of U-shaped openings 50, through which the pledgets 32 of the second set of sutures 28 can be seen.

The cover sheets 34, 38, 42, 46 are constructed of any relatively stiff card-like material, including paper, paperboard and plastic and laminates of these with each other, fabric, or metal foil. Particularly preferred materials are paperboard such as 5 point to 12 point solid bleached sulfate board or 27 pounds per ream bleached Kraft paper. The cover sheets 34, 38, 42, 46, are preferably at least partially coated with a heat sealing film, for example, a low density polyethylene or a polyvinylchloride.

Final assembly of the suture package 10 is performed by lowering a heat sealing die that is positioned above the jig onto the fourth cover sheet 46. The heat sealing die melts the heat sealing film on each of the cover sheets 34, 38, 42, 46, which causes the cover sheets 34, 38, 42, 46 to adhere to each other and to the lower section 16 of the folder 12. Thus, individual multi-compartment pockets 52 are formed in the suture package 10, with each pocket 52 containing one set of two sutures arranged in superimposed compartments.

Sutures are available in different colors, e.g., white and green. In accordance with the present invention, a suture package 10 with multiple sutures 28 preferably utilizes sutures of two different colors arranged in an alternating pattern to allow the scrub nurse to readily distinguish one suture from another. For example, in the embodiment described above in reference to FIGS. 1 through 7, ten double-armed sutures 28 are packaged in the suture package 10. The needle pairs 30 of the ten sutures 28 are arranged in two horizontal rows of five pairs each. An exemplary arrangement of associated suture colors would be, in the top row: white, green, white, green, white, and in the bottom row: green, white, green, white, green. In this manner, the scrub nurse can readily associate the needle pairs 30 with the correct suture 28. By color coding the sutures 28 with alternating, contrasting colors, more sutures 28 can be stored in a package of a given size without causing confusion, and the two needles 30 of a suture 28 can be separated on the needle park 20 without loss of correlation, i.e., identifying that the two needles 30 are attached to the same suture 28. The needle park 20 assists in identification of the individual sutures 28 by separating the needles 30 of each suture vertically. The pledgets 32 at the center of each suture 28 are visible to the scrub nurse through the U-shaped openings 50.

Accordingly, the suture package 10 of the present invention utilizes a serpentine winding method that progresses in the Z direction, i.e., upwards through each layer of the package. The cover sheets extend in the X and Y directions, with each suture loop resting on a cover sheet, such that the suture loop also extends in the X and Y directions. Each suture 28 occupies two superimposed compartments in the pocket 52, with the suture 28 extending in the Z direction as it traverses from the first compartment into the second compartment.

The winding method in which the suture 28 is first placed around the outside of the split pins 26, 27 and then through the split prevents the sutures 28 from being dragged down into an adjacent compartment of the pocket 52 when the package 10 is withdrawn from the suture winding jig. Sutures pulled into adjacent compartments could otherwise lock against one another during dispensing.

The use of cover sheets of different dimensions facilitates winding different length sutures in the Z direction and having the suture 28 end in the desired location, e.g., such that the pledget 32 is visible or is in position to be covered. In this regard, the space between the bottom of the cover sheets and the second pin 27 can contain a loop of suture, i.e., the suture 28 need not be drawn tightly against the pin 27 when looping back in the opposite direction. This variable loop length provides an additional way to control the position of the suture end. Alternating the suture winding to the left and right of the pins 26, 27 decreases the compression pressure of the package 10 upon the sutures 28, facilitating tangle-free dispensing.

At the point in a critical surgery where these products are typically used, there is a rhythm between the scrub nurse and the surgeon as sutures are passed back and forth. As noted above, using alternating green and white colored sutures aids the scrub nurse in identifying the two ends of a single suture and also helps the surgeon identify the suture ends to tie at the surgical site.

The suture package 10 of the present invention enables rapid arming and release of needles, as well as allowing rapid identification of the individual sutures by their coloring. It also prevents sutures from knotting on themselves, on adjacent sutures, on their own pledgets, or on adjacent pledgets. Each of these benefits support the rhythm between the surgeon and the scrub nurse, which shortens the duration of the surgery, thereby promoting successful operations.

Another exemplary embodiment of a suture package fabricated in accordance with the present invention is illustrated in FIGS. 8–15, which depicts a suture package designed for use in connection with a different length suture, e.g., 36 inch sutures, stored in the same size package. Elements illustrated in FIGS. 8–15 which correspond to the elements described above with respect to FIGS. 1–7 have been designated by corresponding reference numerals increased by one hundred. The embodiment of FIGS. 8–15 is designed for use in the same manner as the embodiment of FIGS. 1–7 unless otherwise stated.

Figure 8:
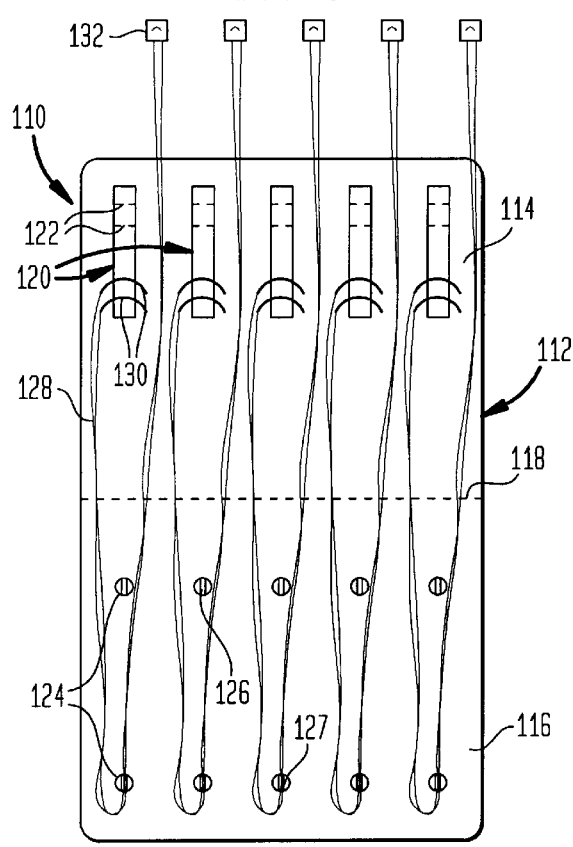
FIGS. 8–15 show diagrammatic views of the steps involved in fabricating a second embodiment of the present invention.

Referring now to FIG. 8, the folder 112 of the suture package 110 is placed onto a suture winding jig (not shown) which includes a plurality of first pins 126 and second pins 127, the pins 126, 127 passing through the corresponding holes 124 in the lower section 116. The needles 130 of a suture 128 are placed into two adjacent slits 122 of the needle park 120. The suture 128 is passed to the left side of the first pin 126 and to the left side of the second pin 127. The suture 128 is then threaded through the slit in the second pin 127 and is passed to the right side of the first pin 126, with the pledget 132 being placed to the right of the needle park 120.

Figure 9:
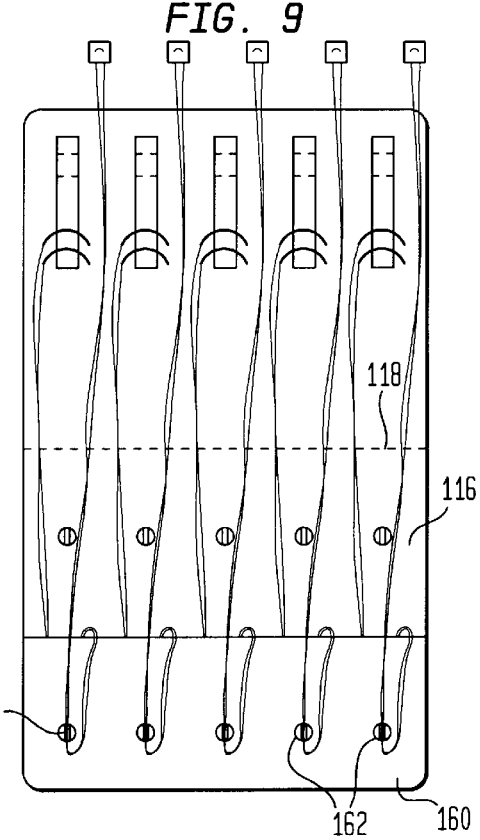

As shown in FIG. 9, a first cover sheet 160 having a plurality of holes 162 is placed onto the jig, with the second pins 127 passing through the holes 162. The first cover sheet 160 is sized such that it covers approximately half of the lower section 116 distal to the fold line 118. The pledget 132 is picked up and the suture 128 is passed to the right of the second pin 127 and on top of the first cover sheet 160. The suture 128 is then threaded through the second pin 127 and passes to the right side of the first pin 126, with the pledget 132 being placed to the right of the needle park 120.

Figure 10:
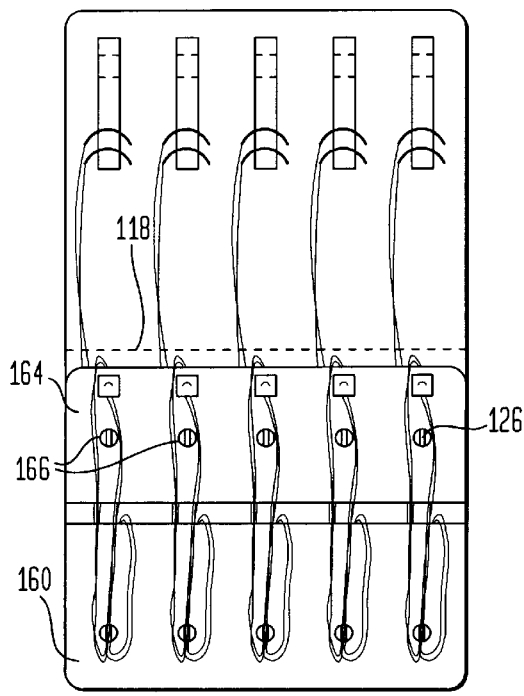

In FIG. 10, a second cover sheet 164 having a plurality of holes 166 is placed onto the jig, with the first pins 126 passing through the holes 166. The first cover sheet 164 is sized such that it covers approximately half of the lower section 116 proximate to the fold line 118. The suture 128 is picked up and passed to the left side of the first and second pins 126, 127 and on top of the first and second cover sheets 160, 164. The suture 128 is then threaded through the second pin 127 and passed to the right of the first pin 126, with the pledget 132 being placed on the second cover sheet 164.

Figure 11:
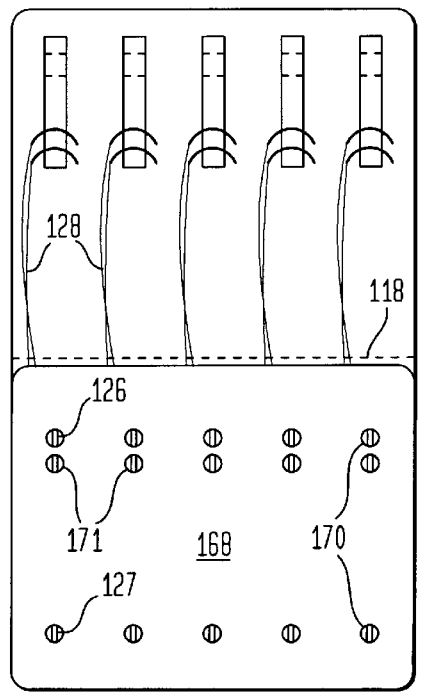

Referring now to FIG. 11, a third cover sheet 168 having a plurality of holes 170 is placed onto the jig. The first and second pins 126, 127 align with the holes 170. The third cover sheet 168 is dimensioned to cover the first and second cover sheets 160, 164 and extends adjacent to the fold line 118 of the folder 112. The third cover sheet 168 covers the sutures 128 and the pledgets 132 of the first set of sutures. An extraneous set of holes 171 is provided in the third cover sheet 168, because the sheet 168 may have a dual use similar to the sheet 34 shown in FIG. 3 and described above in connection with the first embodiment of the present invention.

Figure 12:
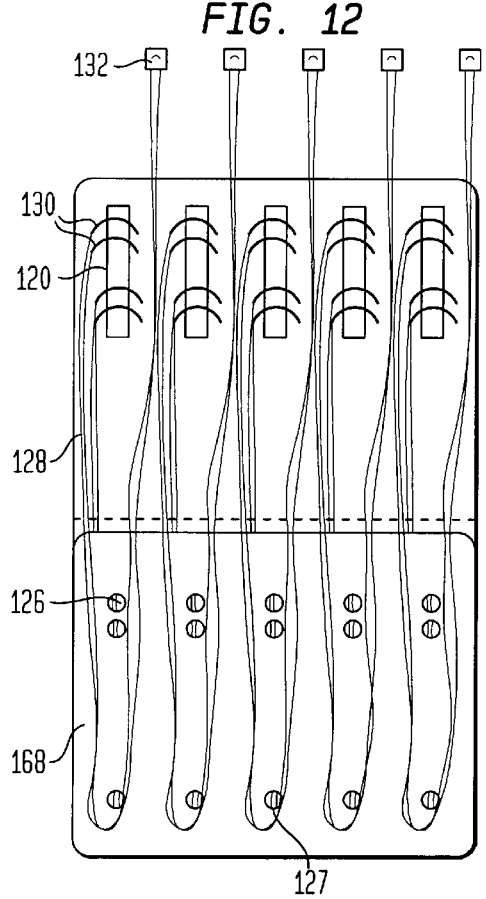

FIG. 12 shows the first step of assembling the second set of sutures 128. The needles 130 of a suture 128 are placed into the two empty, upper slits 122 of the needle park 120. The suture 128 is passed to the left side of the first pin 126, to the left side of the second pin 127, and on top of the third cover sheet 168. The suture 128 is then threaded through the slit in the second pin 127 and is passed to the right side of the first pin 126, with the pledget 132 being placed to the right of the needle park 120.

Figure 13:
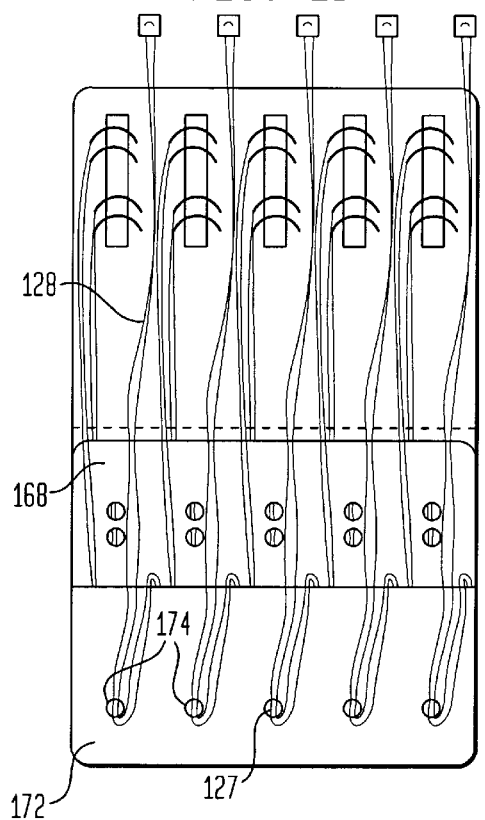

As shown in FIG. 13, a fourth cover sheet 172 having a plurality of holes 174 is placed onto the jig, with the second pins 127 passing through the holes 174. The fourth cover sheet 172 is approximately the same size as the first cover sheet 160, covering half of the third cover sheet 168 distal to the fold line 118. The pledget 132 is picked up and the suture 128 is passed to the right of the second pin 127 and on top of the fourth cover sheet 172. The suture 128 is then threaded through the second pin 127 and passes to the right side of the first pin 126, with the pledget 132 being placed to the right of the needle park 120.

Figure 14:
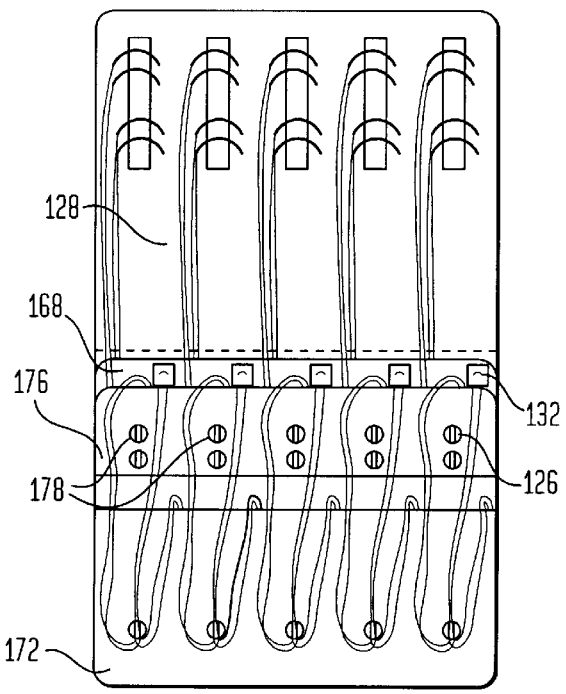

In FIG. 14, a fifth cover sheet 176 having a plurality of holes 178 is placed onto the jig, with the first pins 126 passing through the holes 178. The fifth cover sheet 176 is approximately the same size as the second cover sheet 164, and covers half of the lower section 116 proximate to the fold line 118. The suture 128 is picked up and passed to the left side of the first and second pins 126, 127 and on top of the fourth and fifth cover sheets 172, 176. The suture 128 is then threaded through the second pin 127 and passed to the right of the first pin 126, with the pledget 132 being placed on the third cover sheet 168.

Figure 15:
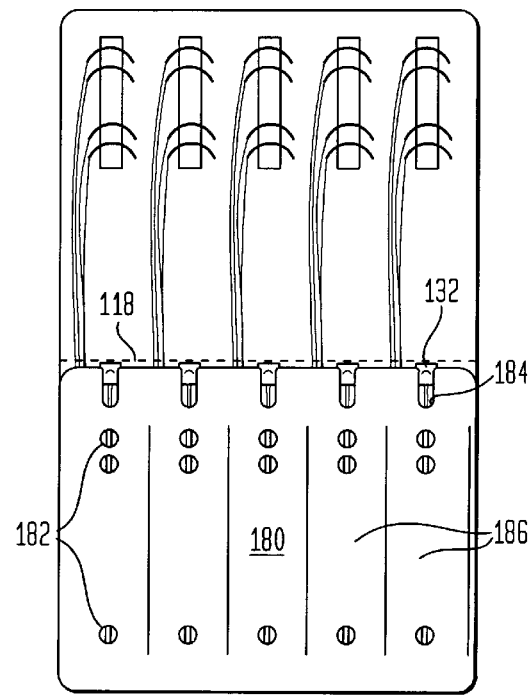

Referring now to FIG. 15, a sixth cover sheet 180 having a plurality of holes 182 is placed onto the jig, with the pins 126, 127 passing through the holes 182. The sixth cover sheet 180 includes a plurality of U-shaped openings 184, through which the pledgets 132 of the second set of sutures 128 can be seen.

The cover sheets 160, 164, 168, 172, 176, 180 have the same or similar compositions as in the previous embodiment and are preferably at least partially coated with a heat sealing film, for example, a low density polyethylene or a polyvinylchloride. As before, final assembly of the suture package 110 is performed by lowering a heat sealing die that is positioned above the jig onto the sixth cover sheet 180 to form individual multi-compartment pockets 186, with each pocket 186 containing one set of two sutures arranged in superimposed compartments.

The suture packages 10, 110 described above may be modified to contain any number of sutures, with the preferred range being between two and ten sutures per package. In many instances, packages containing the correct number of sutures for a particular surgical procedure can be provided and such packages can, if desired, contain an assortment of needle sizes with each size prominently and individually marked on the upper section 14, 114 of the folder 12, 112 adjacent to the needle park 20, 120. In another variation of the suture package 10, 110, the bottom of the package may also be heat sealed, to enclose the pockets 52, 186 on three sides. The cover sheets may also be joined by adhesives or mechanical means as an alternative to heat sealing.

Figure 16:
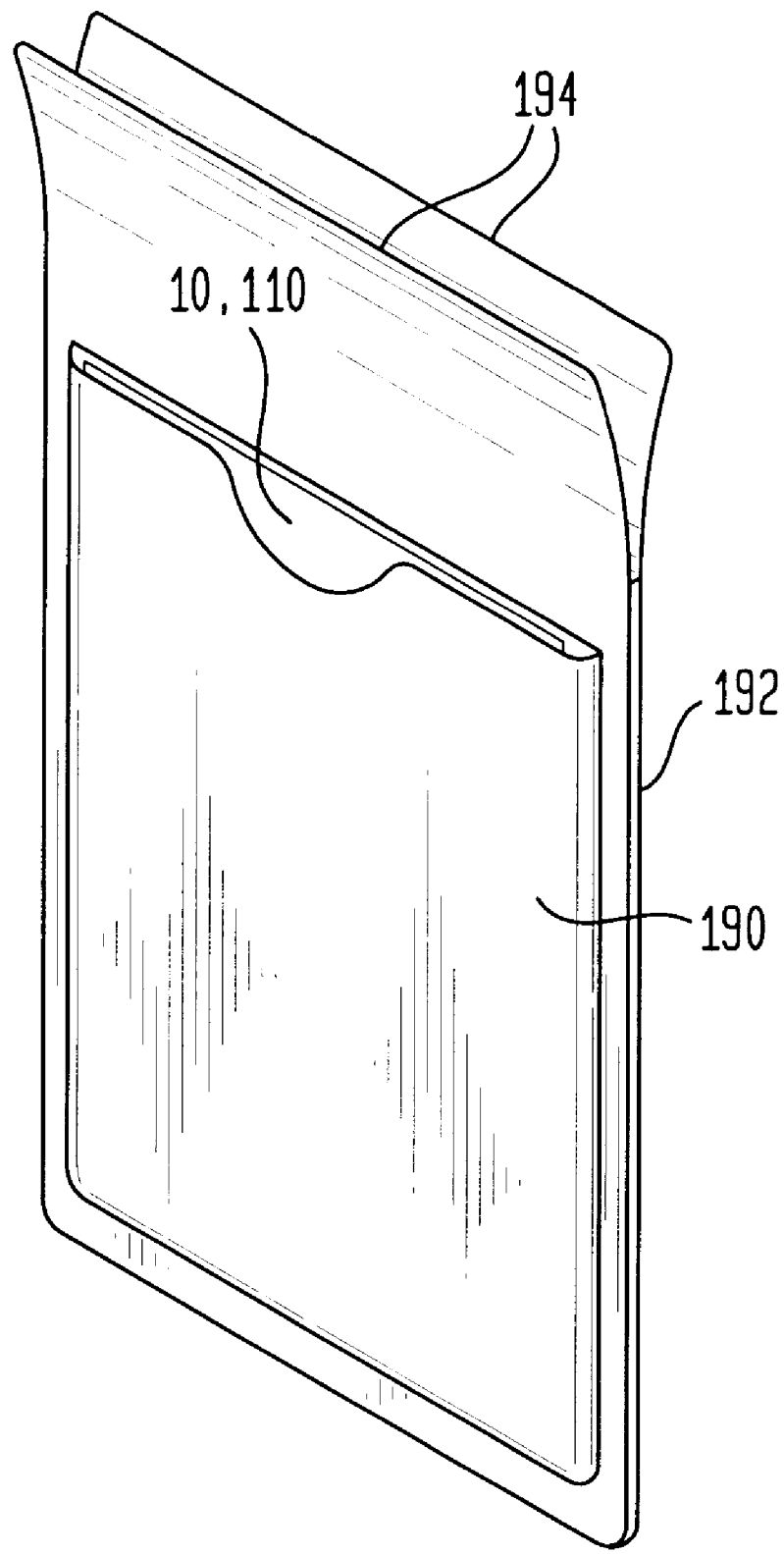
FIG. 16 is a perspective view of a folded suture package according to the present invention in a retaining sleeve and hermetically sealed in a sterile outer envelope.

The suture packages 10, 110 are sterilized after fabrication by radiation, heat, ethylene oxide, or any other convenient and conventional method which is not incompatible with the package or suture materials. Sterile packages are hermetically sealed in an outer envelope wrap to preserve sterility. A folded suture package and retaining sleeve sealed in a transparent, peelable overwrap is shown in FIG. 16, where retaining sleeve 190 surrounds the suture package 10, 110.

An overwrap envelope 192 includes peel flaps 194 at one end for easy opening and access to the sleeve 190. The overwrap envelope 192 is heat sealed around the outer edges using conventional techniques to enclose the sleeve 190.

The pledgets 32, 132 employed in the preparation of the suture packages 10, 110 of the present invention may be made of any biologically compatible, needle pierceable resilient material and of a variety of sizes. In general, rectangular pads about 3 mm by 6 mm by 1–2 mm thick are satisfactory for most surgical procedures. The pledgets 32, 132 may be fabricated of fabric, felt, or any similar cushioning material. One preferred pledget material is a Teflon impregnated polyester felt. While the present invention has been described in terms of packaging sutures with pledgets, the same apparatus, techniques, and teachings can be applied in packaging sutures without pledgets.

While the foregoing description has been directed to a suture package having two suture sets arranged in superimposed compartments, it is possible to construct a suture package according to the present invention that has only one set of sutures or more than two sets of sutures. To construct such a package with one set of sutures, for example in connection with the first embodiment of the present invention, the second cover sheet 38 (as shown in FIG. 4) is substituted with the fourth cover sheet 46 (as shown in FIG. 7) and the package is then heat sealed.

It will be understood that the embodiments described herein are merely exemplary and that a person skilled in the art may make many variations and modifications without departing from the spirit and scope of the present invention. All such variations and modifications are intended to be included within the scope of the invention as defined in the appended claims.

What is claimed is:

1. A suture package, comprising:

a base panel;

a needle park disposed on said base panel;

a first cover sheet positioned on and substantially parallel to said base panel;

a second cover sheet positioned on and substantially parallel to said first cover sheet, said second cover sheet being attached to said first cover sheet and said first cover sheet being attached to said base panel to form a multi-compartment pocket having a first compartment formed between said base panel and said first cover sheet and a second compartment formed between said first cover sheet and said second cover sheet; and a first suture having at least one needle removably retainable in said needle park, said first suture having a first portion positioned in said first compartment and a second portion positioned in said second compartment.

2. A suture package according to claim 1, wherein said first and said second portions of said first suture are loops, said first suture extending around an edge of said first cover sheet proximate to said needle park where said first suture traverses from said first compartment into said second compartment.

3. A suture package according to claim 2, further comprising:

a third cover sheet positioned on and substantially parallel to said second cover sheet;

a fourth cover sheet positioned on and substantially parallel to said third cover sheet, said fourth cover sheet being attached to said third cover sheet and said third cover sheet being attached to said second cover sheet to form a third compartment of said multi-compartment pocket between said second cover sheet and said third cover sheet and a fourth compartment of said multi-compartment pocket between said third cover sheet and said fourth cover sheet; and a second suture having at least one needle removably retainable in said needle park, said second suture having a first portion positioned in said third compartment and a second portion positioned in said fourth compartment, said first and said second portions of said second suture being loops, said second suture extending around an edge of said third cover sheet proximate to said needle park where said second suture traverses from said third compartment into said fourth compartment.

4. A suture package according to claim 3, further including a plurality of said multi-compartment pockets positioned side-by-side, each multi-compartment pocket accommodating two sutures.

5. A suture package according to claim 4, wherein said base panel is divided by a fold line into a first section and a second section, said first section having said needle park, and said first, second, third, and fourth cover sheets being positioned on said second section.

6. A suture package according to claim 5, wherein said needle park includes a plurality of resilient members, each resilient member having a plurality of slits, each slit sized and shaped to receive one needle.

7. A suture package according to claim 3, wherein said first and said second sutures each have two needles, one needle at each end of the suture, both needles of said first and said second sutures retained in said needle park with the associated suture bifolded and positioned in said first and said second compartments and said third and said fourth compartments, respectively.

8. A suture package according to claim 7, wherein said first and said second sutures have different colors, and wherein the needles of said first suture in said needle park are spatially separated relative to each other and relative to the needles of said second suture.

9. A suture package according to claim 8, further including a plurality of said multi-compartment pockets positioned side-by-side, each multi-compartment pocket accommodating two sutures, and wherein adjacent sutures have alternating colors.

10. A suture package according to claim 7, wherein said first and said second sutures each have a pledget, said pledget of said first suture being covered by said second cover sheet, said pledget of said second suture being visible to a user through an opening in said fourth cover sheet.

11. A suture package according to claim 3, wherein at least one of said first and third cover sheets is split into two panels, and wherein a supplementary loop is formed in at least one of said first suture and said second suture, said supplementary loop extending between said two panels and being positioned in said compartment above said split cover sheet.

12. A suture package according to claim 11, wherein said first cover sheet and said third cover sheet are split into two panels, said second portion of said first suture includes a primary loop and said supplementary loop, both said primary and said supplementary loops of said second portion of said first suture being positioned in said second compartment, and wherein said second portion of said second suture includes a second primary loop and a second supplementary loop, both said second primary and said second supplementary loops of said second portion of said second suture being positioned in said fourth compartment.

13. A suture package according to claim 3, wherein said first, second, third, and fourth cover sheets are of varying width to control the length of said first and second portions of said first suture and said second suture, respectively, thereby controlling the position of an end of said first suture and said second suture relative to said first, second, third, and fourth cover sheets.

14. A suture package according to claim 3, wherein the loops of said first and said second sutures are arranged in alternating left and right orientations relative to an axis of symmetry of said pocket, thereby decreasing the cumulative thickness of said looped sutures and decreasing suture-to-suture and suture-to-package friction.

15. A suture package, comprising:
 a base panel;
 a needle park disposed on said base panel;
 a first cover sheet positioned on and substantially parallel to said base panel;
 a second cover sheet positioned on and substantially parallel to said first cover sheet, said second cover sheet being attached to said first cover sheet and said first cover sheet being attached to said base panel to form a multi-compartment pocket having a first compartment formed between said base panel and said first cover sheet and a second compartment formed between said first cover sheet and said second cover sheet; and
 a first suture having at least one needle removably retainable in said needle park, said first suture having a first loop portion extending into said first compartment in the X and Y directions, said first suture then extending in the Z direction from said first compartment into said second compartment wherein a second loop portion of said first suture extends in the X and Y directions.

16. A suture package according to claim 15, further comprising:
 a third cover sheet positioned on and substantially parallel to said second cover sheet;
 a fourth cover sheet positioned on and substantially parallel to said third cover sheet, said fourth cover sheet being attached to said third cover sheet and said third cover sheet being attached to said second cover sheet to form a third compartment of said multi-compartment pocket between said second cover sheet and said third cover sheet, and a fourth compartment of said multi-compartment pocket between said third cover sheet and said fourth cover sheet; and
 a second suture having at least one needle removably retainable in said needle park, said second suture having a first loop portion extending into said third compartment in the X and Y directions, said second suture then extending in the Z direction from said third compartment into said fourth compartment, wherein a second loop portion of said second suture extends in the X and Y directions, said first and said second sutures winding in a generally serpentine manner in the Z direction as each suture traverses from said needle park into said first and said second compartments and said third and said fourth compartments, respectively.

17. A suture package according to claim 16, further including a plurality of said multi-compartment pockets positioned side-by-side, each multi-compartment pocket accommodating two sutures, and wherein adjacent sutures have alternating colors, and wherein each suture has two needles, one needle at each end of the suture with both needles stored in said needle park, the needles being spatially separated relative to each other and relative to the needles of the other sutures in said needle park.

18. A method for assembling a suture package including a base panel having a plurality of holes and a needle park, a first cover sheet having a plurality of holes and an edge proximate to the needle park, a second cover sheet having a plurality of holes, and a first suture having at least one needle, comprising the steps of:
 (a) placing the base panel on a suture winding jig having a first split pin and a second split pin, the first and second split pins passing through the holes of the base panel;
 (b) affixing the at least one needle of the first suture to the needle park;
 (c) passing the first suture to the left side of the first split pin, to the left side of the second split pin, through the split in the second split pin, and through the split in the first split pin, to form a first loop in the first suture;
 (d) placing the first cover sheet on the suture winding jig, such that the first and second split pins extend through the holes in the first cover sheet, the first cover sheet covering a portion of the first loop in the first suture;
 (e) passing the first suture around the edge of the first cover sheet and on top of the first cover sheet, to the right side of the first split pin, to the right side of the second split pin, through the split in the second split pin, and through the split in the first split pin, to form a second loop in the first suture;
 (f) placing the second cover sheet on the suture winding jig, such that the first and second split pins extend through the holes in the second cover sheet, the second cover sheet at least partially covering the second loop in the first suture;
 (g) attaching the second cover sheet to the first cover sheet, and attaching the first cover sheet to the base panel, to form a multi-compartment pocket such that the first and second loops of the first suture each occupy separate compartments in the multi-compartment pocket; and
 (h) removing the suture package from the winding jig.

19. The method according to claim 18, wherein the suture package further includes a third cover sheet having a plurality of holes and an edge proximate to the needle park, a fourth cover sheet having a plurality of holes, and a second suture, the first and second sutures each having two needles, one needle at each end of the suture, further comprising the following steps after step (f) and before step (g):
 (i) affixing the two needles of the second suture to the needle park;
 (j) passing the second suture on top of the second cover sheet and to the left side of the first split pin, to the left side of the second split pin, through the split in the second split pin, and through the split in the first split pin, to form a first loop in the second suture;
 (k) placing the third cover sheet on the suture winding jig, such that the first and second split pins extend through the holes in the third cover sheet, the third cover sheet covering a portion of the first loop in the second suture;
 (l) passing the second suture around the edge of the third cover sheet and on top of the third cover sheet, to the right side of the first split pin, to the right side of the second split pin, through the split in the second split pin, and through the split in the first split pin, to form a second loop in the second suture;
 (m) placing the fourth cover sheet on the suture winding jig, such that the first and second split pins extend through the holes in the fourth cover sheet, the fourth cover sheet at least partially covering the second loop of the second suture; and (n) attaching the fourth cover sheet to the third cover sheet, and attaching the third cover sheet to the second cover sheet to form additional compartments in the multi-compartment pocket, the first and second loops of the second suture each occupying separate compartments of the multi-compartment pocket.

20. The method according to claim 19, wherein step (e) includes dragging the portion of the second loop of the first suture that is proximate to the second split pin away from the second split pin in the direction opposite the needle park, thereby positioning the end of the second loop of the first suture in a desired location on the first cover sheet; and step (l) includes dragging the portion of the second loop of the second suture that is proximate to the second split pin away from the second split pin in the direction opposite the needle park, thereby positioning the end of the second loop of the second suture in a desired location on the third cover sheet.

* * * * *